United States Patent
Mundkinajeddu et al.

(10) Patent No.: US 6,977,294 B2
(45) Date of Patent: Dec. 20, 2005

(54) **PROCESS FOR ISOLATION OF EUPALITIN FROM *BOERHAVIA DIFFUSA***

(75) Inventors: Deepak Mundkinajeddu, Jammu (IN); Lila Ram Manahas, Jammu (IN); Rakesh Maurya, Jammu (IN); Sukhdev Swami Handa, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/099,292

(22) Filed: Mar. 13, 2002

(65) Prior Publication Data
US 2003/0175373 A1 Sep. 18, 2003

(51) Int. Cl.$^7$ .................. C07H 17/00; A61K 35/78
(52) U.S. Cl. .................. 536/8; 536/127; 536/128; 536/4.1; 424/195.1; 424/180; 549/403
(58) Field of Search .................. 536/8, 127, 128, 536/4.1; 424/195.1, 180; 549/403

(56) References Cited

U.S. PATENT DOCUMENTS

| | | | | |
|---|---|---|---|---|
| 6,071,883 A | * | 6/2000 | Chen et al. | 514/25 |
| 6,084,080 A | * | 7/2000 | Zeng et al. | 536/8 |
| 6,777,392 B2 | * | 8/2004 | Maurya et al. | 514/27 |

OTHER PUBLICATIONS

Li et al., J. Nat. Prod. 59, 1015–1018, 1996.*
Li et al. "Effects on cultured neonatal mouse calvaria of the flavonoids isolated from *Boerhaavia repens*." J. Nat. Prod. 59, 101 1018, 1996.*
Ramabhimaiah et al. "pharmacological investigations on the water soluble fraction of methanol extract of *Boerhaavia diffusa* root." Indian Drugs, vol. 21., No. 8, 343–344, May 1984.*
Bezuidenhoudt et al. "Flavonoid analogues from Pterocarpus species." Phytochemistry, vol. 26, No. 2, 531–535, 1987.*
A.K.S. Rawat et al., *J. Ethnopharmacology*, 1997, 56:61–66.
B.K. Chandan et al., *J. Ethnopharmacology*, 1991, 31:299–307.
J.A. Ojewole, *Fitoterapia*, 1985, 56:31–36.
Ken R. Markham et al., *The Flavonoids: Advances in Research*, 1982, Chapter 2.
A, Bramadhayalaselvam et al., *J. Econ. Tax. Bot.*, 1994, 18(2):499–500.
R.P. Singh et al., *J. Res. Ed. Ind. Med.*, 1992, 29–36.
S. Ramabhimaiah et al., *Indian Drugs*, 1984, 21(8):343–344.
R.K. Seth et al., *Indian Drugs*, 1986, 23(10):583–584.
Anubha Singh et al., *Indian Drugs*, 1988, 26(1):10–13.
Aruna Mathur et al., *Geobios*, 1983, 2(1):35–38.
K. Hansen et al., *In Vitro Screening of Indian Medicinal Plants* . . . , Chapter 26, pp. 263–273, 1995.

Nzunzu Lami et al., *Chem. Pharm. Bull.*, 1991, 39(6):1551–1555.
Shigetoshi Kadota et al., *Chem. Pharm. Bull.*, 1989, 37(12):3214–3220.
Nzunzu Lami et al., *Chem. Pharm. Bull.*, 1990, 38(6):1558–1562.
P.A. Akah et al., *Fitoterapia*, 1993, vol. LXIV, No. 1, 42–44.
S.K. Varma, *Biol. Bull. Ind.*, 1983, 5(1):50–52.
M. Barthwal et al., *Advances in Contraception*, 1991, 7:67–76.
S. Kola Adesina, *Quart. J. Crude Drug Res.*, 1979, 17(2):84–86.
D.R. Gupta et al., *Ind. J. Chem.*, 1984, 23B:682–684.
Nzunzu Lami et al., *Chem. Pharm. Bull.*, 1991, 39(7):1863–1865.
S. Kadota et al., *J. Pharma. Sci.*, 1987, 76(11).
Anubha Singh et al., *Planta Med.*, 1991, 57:315–316.
M. Barthwal et al., *Advances in Contraception*, 1990, 6:113–124.
Maniruddin Ahmed et al., *Phytochemistry*, 1990, 29(5):1709–1710.
G.K. Jain et al., *Ind. J. Chem.*, 1989, 28B:163–166.
Bahar Ahmed et al., *Phytochemistry*, 1992, 31(12):4382–4384.
Khalid Aftab et al., *Quart. J. Sci. Med.*, 1996, 39(1):44–54.
P. Goswami et al., *J.R.A.S.*, 1992, 13(1–2):48–55.
P. Goswami et al., *J.R.A.S.*, 1991, 13(3–4):135–140.
Jianxin et al., *J. Nat. Prod.*, 1996, 59:1015–1018.

(Continued)

*Primary Examiner*—James O. Wilson
*Assistant Examiner*—Devesh Khare
(74) *Attorney, Agent, or Firm*—Morgan & Finnegan, LLP

(57) ABSTRACT

The present invention relates to a process of isolation of bioactive eupalitin (3-O-O-D-galactopyranoside) of formula 1 possessing anti-osteoporosis activity by extraction of powdered leaves of *Boerhaavia diffusa*, with better yield:

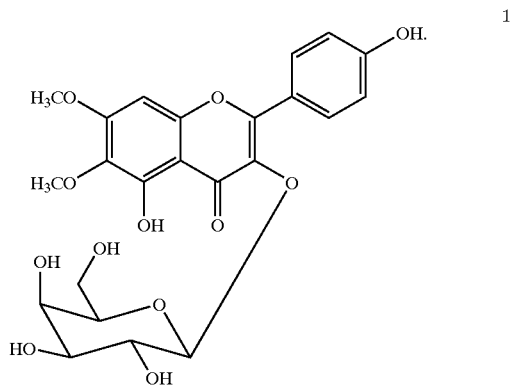

5 Claims, No Drawings

OTHER PUBLICATIONS

R.K. Anand, *Med. & Aromatic Plants Abstr.*, 1996, 18(5):496.

S.K. Varma, *Med. & Aromatic Plants Abstr.*, 1984, 6(2):92.

K. Szendrei et al., *Med. & Aromatic Plants Abstr.*, 1996, 18(5):529.

Mathur A. Bhandari, *Med. & Aromatic Plants Abstr.*, 1983, 5(2):100.

K.K. Chakraborti et al., *Indian Drugs*, 1989, 27(3):161–166.

Subrata De et al., *Indian Drugs*, 1993, 30(8):355–363.

\* cited by examiner

PROCESS FOR ISOLATION OF EUPALITIN FROM *BOERHAVIA DIFFUSA*

FIELD OF THE INVENTION

The present invention relates to a process for isolation of bioactive eupalitin from *Boerhavia diffusa*. More particularly, the present invention relates to a process of isolation of bioactive eupalitin (3-O-β-D-galactopyranoside) of formula 1 possessing anti-osteoporosis activity by extraction of powdered leaves of *Boerhavia diffusa*, with better yield

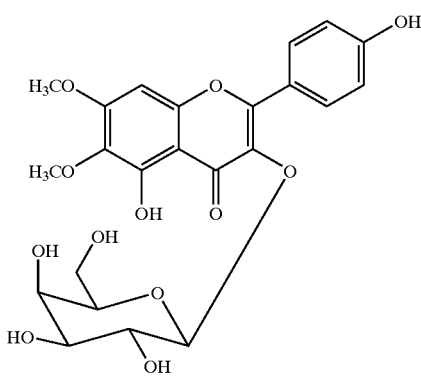

BACKGROUND OF THE INVENTION

*Boerhavia diffusa* Linn. (Syn. *Boerhavia repens* Linn., *Boerhavia procumbens* Roxb.; Family *Nyctaginaceae*) popularly known as Punarnava' is an important rejuvenative drug used in Ayurveda. It is widely distributed throughout India and flourishes during rainy season. The aerial parts then disappear but revive or sprout again next year [Sivarajan, V. V. and Balachandran, I. *Ayurvedic drugs and their plant sources*; Oxford & IBH publishing Co. Ltd., New Delhi, 1994]. Dried matured whole plant constitutes the drug in Indian Herbal Pharmacopoeia [Handa, S. S., Deepak, M. and Mangal, A. K. *Indian Herbal Pharmacopoeia*, Regional Research Laboratory, Jammu & Indian Drug Manufacturers Association, Mumbai, 1998, Vol. 1] which also describes its salient macroscopic and microscopic features.

Biodiversity, tribal association [Anand, R. K. Flora and Fauna 1, 167–170 (1995). *Medicinal & Aromatic Plants Abstracts* 18, 2620 (1996)] and variants [Mathur, A. and Bhandari, M. M. *Geobios New Reports*, 2, 35–38 (1983)). *Medicinal & Aromatic Plants Abstracts* 5, 0643 (1983), Varma, S. K. Biological Bulletin of India 5, 50–52 (1983). *Medicinal & Aromatic Plants Abstracts* 6, 0467 (1984)] of *Boerhavia diffusa* and chemotaxonomic findings [Bramadhayalaselvam, A. and Rajasekaran, K. *Journal of Economic and Taxonomic Botany,* 18, 499–500 (1994)] in *Nyctaginaceae* have been discussed. Many rotenoids have been isolated from the roots of the plant [Ahmed, M., Datta, B. K. and Rouf, A. S. S. *Phytochemistry* 29, 1709–1710 (1990); Kadota, S., Lami, N., Tezuka, Y. and Kikuchi, T. *Chemical and Pharmaceutical Bulletin* 37, 3214–3220 (1989); Lami, N., Kadota, S., Tezuka, Y. and Kikuchi, T. *Chemical and Pharmaceutical Bulletin* 38, 1558–1562 (1990); Lami, N., Kadota, S. and Kikuchi, T. *Chemical and Pharmaceutical Bulletin* 39, 1863–1865 (1991)]. These include a series of boeravinones viz., boeravinone A, boeravinone B, boeravinone C, boeravinone D, boeravinone E and boeravinone F. Punarnavoside, a phenolic glycoside, is reportedly present in roots [Jain, G. K. and Khanna, N. M. *Indian Journal of Chemistry* 28B, 163–166 (1989); Seth, R. K., Khanna, M., Chaudhary, M. Singh, S. and Sarin, J. P. S. *Indian Drugs* 23, 583–584 (1986)].

Three flavonol glycosides viz., eupalitin 3-O-β-D-galactopyranosyl-(1→2)-R-D-glucopyranoside, eupalitin 3-O-β-D-galactopyranoside and 6-methoxykaempferol 3-O-β-D-(1→6) robinoside from the *Boerhaavia repens* whole plant [LL J., LL H., Kadota, S. and Namba, T. *Journal of Natural Products* 59, 1015–1018 (1996)] and a C-methyl flavone have been isolated from *Boerhaavia diffusa* roots [*Indian Journal of Chemistry* 23B, 682–684 (1984)]. Also isolated from *Boerhaavia diffusa* roots are two lignans viz., liriodendrin and syringaresinol mono-β-D-glycoside [Lami, N., Kadota, S., Kikuchi, T. and Momose, Y. *Chemical and Pharmaceutical Bulletin* 39, 1551–1555 (1991)]. Presence of a purine nucleoside hypoxanthine 9-L-arabinose [Ojewole, J. A. O. and Adesina, S. K. *Fitoterapia* 56, 31–36 (1985)] a dihydroisofuroxanthone-borhavine [Ahmed, B. and Yu, C. P. *Phytochemistry* 31, 4382–4384 (1992)] and phytosterols [Kadota, S., Lami, N., Tezuka, Y. and Kikuchi, T. *Chemical and Pharmaceutical Bulletin* 37, 3214–3220 (1989); Kadota, S., Lami, N., Tezuka, Y. and Kikuchi, T. *Journal of Pharmaceutical Sciences* 76, S201 (1987)] from the plant are reported.

Hepatoprotective property of *Boerhavia diffusa* has been investigated and confirmed by different research workers [Chakraborti, K. K. and Handa, S. S. *Indian Drugs* 27, 161–166 (1989); Chandan, B. K., Sharma, A. K. and Anand, K. K. Journal of *Ethanopharmacology* 31, 299–307 (1991); Rawat, A. K., Mehrotra, S., Tripathi, S. C. and Shome, U. *Journal of Ethanopharmacology* 56, 61–66 (1997); De, S., Ravishankar, B. and Bhavsar, G. C. *Indian Drugs* 30, 355–363 (1993)]. The plant possesses potent antifibrinolytic and antiinflammatory activities and is recommended for the treatment of IUD menorrhagia [Barthwal, M. and Srivastava, K. *Advances in Contraception* 7, 67–77 (1991); Barthwal, M. and Srivastava, K. *Advances in Contraception* 6, 113–124 (1990)]. *Boerhaavia diffusa* is also reported to possess antihypertensive properties [Ramabhimaiah, S., Stalin, D. and Kalaskar, N. J. *Indian Drugs* 21, 343–344 (1984)] for which both its angiotensin converting enzyme inhibition [Aftab, K., Usmani, S. B. and Ahmad, S. I. *Hamdard Medicus* 39, 44–54 (1996); *Medicinal & Aromatic Plants Abstracts* 18, 2920 (1996)] and $Ca^{2+}$ channel blocking effects [Hansen, K., Nyman, U. Smith, U. W., Andersen, A., gudiksen, L. Rajasekharan, S and Pushpangadan, P. *Glimpses of Indian Ethnopharmacology* (ed. Pushpangadan, P.) 263–273 (1995)] may be responsible. The drug's usefulness in nephritic syndrome has been demonstrated in albino rats [Singh, A., Singh, R H., Singh, R G., Misra, N., Vrat, S., Prakash, M. and Singh, N. *Indian Drugs* 26, 10–13 (1988)] as well as in humans [Singh, R. P., Shukla, K. P., Pandey, B. L., Singh, R. G., Usha and Singh, R. H. *Journal of Research and Education in Indian Medicine* 11, 29–36 (1992)]. Purified extracts of the plant increased amylase [Goswami, P. and Sharma, T. C. *Journal of Research in Ayurveda and Siddha* 13, 48–55 (1992)] and ATPase [Goswami, P. and Sharma, T. C. *Journal of Research in Ayurveda and Siddha* 13, 135–140 (1992)] activities while decreasing catalase activities in vitro. Roots of the plant also exhibited anticonvulsant properties [Adesina, S. K. *Quarterly Journal of Crude Drug Research* 17, 84–86 (1979); Akah, P. A. and Nwambie, A. I. *Fitoterapia* 64, 42–44 (1993). The drug has been found to be devoid of tetratogenic effect [Singh, A., Singh, R G., Singh, R. H., Misra, N. and Singh, N. *Planta*

*Medica* 57, 315–316 (1991)]. Punarnavoside had antifibrinolytic activity in monkeys [Iain, G. K. and Khanna, N. M. *Indian Journal of Chemistry* 28B, 163–166 (1989). Liriodendrin blocked Ca²⁺ channel in frog heart single cells [Lami, N., Kadota, S., Kikuchi, T. and Momose, Y. *Chemical and Pharmaceutical Bulletin* 39, 1551–1555 (1991)] and hypoxanthine 9-L-arabinoside produced depressor and negative chronotropic effects in rats and cats [Ojewole, J. A. O. and Adesina, S. K. *Fitoterapia* 56, 31–36 (1985)]. A methanol extract from the whole plant of *Boerhaavia repens* was found to inhibit bone resorption induced by parathyroid hormone (PTH) in tissue culture [LL J., LL H., Kadota, S. and Namba, T. *Journal of Natural Products* 59, 1015–1018 (1996)]. Bioactivity guided fractionation of the methanol extract indicated the concentration of activity in the n-butanol soluble fraction. From the n-butanol soluble fraction eupalitin 3-O-β-D-galactopyranoside was isolated and was found to have significant (p<0.001) inhibition of bone resorption induced by parathyroid hormone (PTH) in tissue culture. The activity shown by eupalitin 3-O-β-D-galactopyranoside was more than that exhibited by lpriflavone, a clinically used natural product derivative for the treatment of osteoporosis in Japan and Italy, under identical conditions.

The compound eupalitin 3-O-β-D-galactopyranoside was isolated by Li et al [LL J., Li, H., Kadota, S. and Namba, T. *Journal of Natural Products* 59, 1015–1018 (1996)] as follows: The shade-dried *Boerhaavia repens* whole plant (1.2 kg) was chopped into small pieces and refluxed with methanol for 3 h (900 ml×2). The total filtrate was evaporated under reduced pressure to obtain a dark green mass, and this extract was suspended in distilled water and partitioned with chloroform and n-butanol successively. The n-butanol soluble fraction was purified repeatedly by preparative TLC to yield eupalitin 3-O-β-D-galactopyranoside (14.4 mg, 0.0012%).

Li et al Process has the Following Major Disadvantages

1. The process employs *Boerhaavia repens* whole plant, which contains lesser amounts.
2. 6 Hours reflux with methanol is not sufficient for complete extraction of eupalitin 3-O-β-D-galactopyranoside.
3. Methanol extract is suspended in distilled water and partitioned with chloroform and n-butanol successively. During partitioning with chloroform eupalitin 3-O-β-D-galactopyranoside gets distributed into chloroform layer also, thus reducing the final yield of compound of formula 1 from butanol fraction.
4. The compound was purified by expensive, tedious and time consuming Preparative Thin Layer Chromatography yielding minute quantity of eupalitin 3-O-β-D-galactopyranoside (14.4 mg, 0.0012%). This process of isolation, being tedious and uneconomical, can not be accepted for the commercial production of eupalitin 3-O-β-D-galactopyranoside.

Osteoporosis is one of the major problems in our aging society. Osteoporosis results in bone fracture in older members of the population, especially in post-menopausal women. In traditional medicine, many natural crude drugs have potential use to treat bone diseases. Since eupalitin 3-O-β-D-galactopyranoside exhibits greater anti-osteoporosis activity than ipriflavone, a natural product derivative being used clinically for this purpose, large amounts of eupalitin 3-O-β-D-galactopyranoside are required.

Only a minute quantity of this compound (14.4 mg from *Boerhaavia repens* dried whole plant, 1.2 kg) is isolated using the process developed by Li et al [LL J., LL H., Kadota, S. and Namba, T. *Journal of natural Products* 59, 1015–1018 (1996)]. Therefore, there is an urgent need to develop an efficient less time consuming process for the large-scale isolation of eupalitin 3-O-β-D-galactopyranoside to enable its easy availability for further studies.

OBJECTS OF THE INVENTION

The main object of the present invention is to provide a process for the isolation of bioactive eupalitin 3-O-β-D-galactopyranoside having the formula 1 from *Boerhaavia diffusa*.

Another object of the invention is to identify the plant part of *Boerhaavia diffusa* that provides maximum yield of 3-O-β-D-galactopyranoside of formula 1.

Another object of the present invention is to provide a novel process for the isolation of eupalitin (3-O-β-D-galactopyranoside) wherein the process is simple and results in quick isolation of the desired product.

It is another object of the invention to provide a process wherein highly economical raw material, which is abundant in nature is utilized.

It is a further object of the invention to provide a process that is ideal for scale up and does not prescribe any tedious chromatographic procedure for purification and isolation of the compound as in the prior art where expensive, tedious and time consuming preparative thin layer chromatography is required.

SUMMARY OF THE INVENTION

The above and other objects of the invention are achieved by the novel process of extraction of eupalitin (3-O-β-D-galactopyranoside) described herein with yields of about 300 times more than reported in the art from the powdered leaves of *Boerhaavia diffusa*.

Accordingly the present invention provides a process for the isolation of 3-O-β-D-galactopyranoside of the formula 1 from *Boerhavia diffusa* comprising (a) powdering the plant material,
(b) preparing an extract of the powdered plant material with a protic solvent
(c) concentrating the extract obtained in step (b) above,
(d) triturating the above said concentrated extract successively with organic solvents in order of increasing polarity to get a rich bioactive fraction,
(e) crystallization and re-crystallization of the bioactive fraction with methanol to obtain eupalitin 3-O-β-D-galactopyranoside,

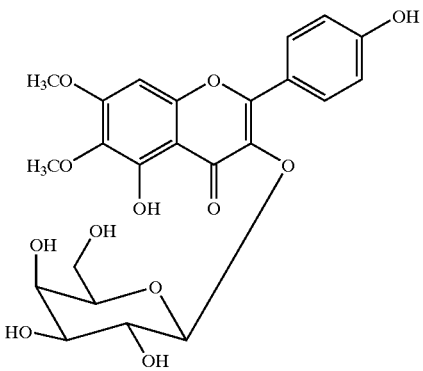

In one embodiment of the invention, the plant material is selected from aerial parts of the plant.

In a further embodiment of the invention, the plant material is selected from the group comprising of the leaves and the stem of *Boerhaavia diffusa* and a combination thereof.

In another embodiment of the invention, the protic solvent used for the extraction in step (b) is selected from the group consisting of rectified spirit, methanol and aqueous methanol.

In a further embodiment of the invention, the organic solvent used in step (d) is selected from the group consisting of hexane, chloroform, ethyl acetate, methanol, ethanol and aqueous methanol.

In another embodiment of the invention, the process of isolation of 3-O-β-D-galactopyranoside of formula 1 from *Boerhaavia diffusa* comprises extracting the powdered leaves thereof in a polar solvent selected from the group consisting of rectified spirit, methanol and aqueous methanol in glass percolator or in Soxhlet extractor, removing fatty non-polar constituents by trituration with an organic solvent selected from hexane, dichloromethane, chloroform and ethyl acetate to get rich bioactive fraction, crystallization with a polar solvent to obtain 3-O-β-D-galactopyranoside (1) in the range 0.25–0.5% w/w.

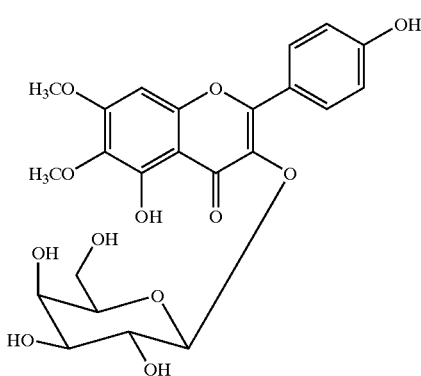

DETAILED DESCRIPTION OF THE INVENTION

The process of the present invention overcomes disadvantages of the prior art since:

1. Aerial parts such as leaves of *Boerhavia diffusa* collected from specific locations identified herein are used (containing the maximum amount of the compound and as established by analyzing the samples of the plant collected during three years).
2. The process prescribes hot continuous extraction (Soxhlet extraction) ensuring complete extraction of compound of formula 1. As compound of formula 1 is not highly soluble in methanol reported prior art process is results in incomplete extraction.
3. Trituration is prescribed of the residue obtained by rectified spirit extraction with hexane and chloroform in which compound of formula 1 does not get partitioned into chloroform layer, thus ensuring the presence of total extracted compound of formula 1 in the rectified spirit fraction after triturition for isolation.
4. The compound is purified by direct crystallization from the residue obtained after triturition described in 3, making it the simplest, quickest, highly economically viable, scale up compatible for commercial utilization and novel method for the isolation of compound of formula 1 with an yield upto 0.4% which is more than 300 times the yield reported by Li et al.

Osteoporosis is one of the major problems in our aging society. Osteoporosis results in bone fracture in older members of the population, especially in post-menopausal women. In traditional medicine, there are many natural crude drugs that have the potential for use to treat bone diseases. Since 3-O-β-D-galactopyranoside exhibits greater anti-osteoporosis activity than ipriflavone, a natural product derivative being used clinically for this purpose, large amounts of eupalitin 3-O-β-D-galactopyranoside are required. Only a minute quantity of this compound (14.4 mg from *Boerhaavia repens* dried whole plant, 1.2 kg) was isolated using the process developed by Li et al [LL J., LL H., Kadota, S. and Namba, T. *Journal of Natural Products* 59, 1015–1018 (1996)].

A preliminary screening for the amount of eupalitin 3-O-β-D-galactopyranoside (1) in whole plant samples of *Boerhaavia diffusa* collected from eight phytogeographically different regions of India indicated significant quantitative variations (Table 1).

TABLE 1

HPLC determination of eupalitin 3-0-D-D-galactopyranoside (1) in different samples of *B. diffusa* and in different parts of Jammu sample.

| Region of collection India | Collection period | Constituents, Means % w/w) |
|---|---|---|
| Jammu J&K | August 1996 | 0.130 |
| Ramgarh (Bihar) | September 1997 | 0.070 |
| Ranchi (Bihar) | September 1997 | 0.049 |
| Chandigarh | September 1997 | 0.004 |
| Mangalore (Karnataka) | December 1997 | 0.062 |
| Trivandrum (Kerala) | December 1997 | 0.016 |
| Kasaragod (Kerala) | December 1997 | 0.001 |
| Suratkal (Karnataka) | December 1997 | ND |
| Different parts of Jammu sample | | |
| Leaves | August 1996 | 0.239 |
| Stems | | 0.045 |
| Flower | | 0.031 |
| Roots | | ND |

$^e$n = 3, standard deviation of mean values were in the range 0.000–0.005; ND = not detected Interestingly the Jammu sample was found to possess maximum amount (almost double than the next sample containing maximum amount i.e. Ramgarh sample). In addition, compound 1 was found to be concentrated in leaves (5 times the amount present in stems) and was absent in the roots.

The results also emphasized the need to have standardized extracts containing known amounts of compound of formula 1 in any further study of *B. diffusa* for inhibition of PTH-stimulated bone resorption. Furthermore, the extract of leaves may be preferred to that of whole plant as the former is rich in eupalitin 3-O-β-D-galactopyranoside (1), the active constituent.

The process for the isolation of bioactive eupalitin 3-O-(3-D-galactopyranoside of formula 1 from *Boerhavia diffusa* comprises:

(a) powdering the plant material by known methods,
(b) concentrating the alcoholic extract by conventional method,
(c) triturating the above said extracts successively with organic solvent in order of increasing polarity get rich bioactive fraction
(d) crystallization and re crystallization with methanol by conventional methods to obtain eupalitin 3-O-β-D-galactopyranoside.

Characterization of Compound 1

Compound 1 obtained as yellow amorphous solid, $[a]D$-26.6 (c 0.03, methanol). UV spectrum of compound of formula 1 had bands (Band I-342nm, Band-II-270nm) characteristic of flavonoids. Bathochromic shift (+45nm) of band-I upon addition of sodium methoxide indicated the presence of hydroxyl group in 3 position. $^1$H NMR signals at 6.88 (2H,d,J=9Hz) and 8.11 (2H,d,J=9 Hz) strongly suggested the presence of 4' OH with no other substitutions in B ring. The $^1$H NMR spectrum also revealed the presence of two methoxyl groups (δ 3.75, 3.93, 3H each, s), a hydroxyl group at 5 position (δ 12.56, br s) and an anomeric sugar proton (δ 5.41.1H,d,J=7.5 Hz). Literature comparison of $^{13}$C signal$^s$ of sugar led to its identity as galactose [Markham, K–R.; Chari, V. M. Carbon-13 NMR spectroscopy of flavonoids. In *The flavonoids: Advances in Research*; Harbome, J. B.; Mabry, T. J., Eds; Chapman & Hall: London, 1982; Chapter 2, pp 19–134)] Molecular weight of 1 was found to be 492 (from FAB MS) and that of aglycone to be 330 (from El-MS). Thus the aglycone had three hydroxyl groups, one of which bonded to galactose and two methoxyl groups which was confirmed by the formation of hexa acetate. Since free hydroxyls at 5 and 4' positions were already established, the glycosidic linkage at three position became evident. Positions of two methoxyl groups were assigned C-6 and 7 positions as the NMR signal of the proton (δ 6.86, 1H, s) did not show any shift upon acetylation of 5-OH, thus ruling out the possibility of its presence in 6 position. Furthermore, $^{13}$C signals at δ 92.0 (C-6), 60.9 (6-OCH$_3$) and 57.3 (7-OCH$_3$) were in agreement with the values proposed for similar substitutions in B ring (Horie, T.; Ohtsuru, Y.; Sbibata, K.; Yamashita, K.; Tsukayama, M.; Kawamura, Y. *Phytochemistry* 47, 865–874(1998).]

Thus the structure of 1 was deduced as 5,4'-dihydroxy 6, 7-dimethoxy-flavonol-3-O-β-D-galactoside (eupalitin or 3-O-β-D-galactopyranoside). The higher yield of compound 1 from the leaves of Jammu sample was further confirmed and standardized by the fact that similar yields of compound 1 (~0.2 upto 0.4%) was obtained from the plant collected from Jammu in 1996, 1998 and 1999. The plant is abundantly available in Jammu region during and after the rainy season (July–October). On the other hand, samples collected from other places of India contained lesser amounts of 1 as determined by HPLC (Table 1) thus making them less suitable and less economical raw materials for the isolation of 1.

Thus the location of collection of the raw material (*Boerhavia diffusa*), extraction and process of isolation of 1 has been standardized for maximum yield of the compound. The process being simple and novel is particularly useful for quick isolation of the compound from the plant for all purposes.

The process for the isolation of bioactive eupalitin 3-O-β-D-galactopyranoside (1) from *Boerhavia diffusa* comprises:

(a) powdering the plant material,
(b) preparing the alcoholic extract of the plant material by hot continuous extraction in a Soxhlet apparatus,
(c) concentrating the alcoholic extract,
(d) successively triturating [trituration means shaking the extract with the solvent] the alcoholic extract with hexane, dichloromethane, chloroform or ethyl acetate, to get rich bioactive fraction
(e) crystallization and re crystallization with polar solvents furnished eupalitin 3-O-R-D-galactopyranoside.

The yield of 1 obtained by the process of the invention employing raw material collected from appropriate location, the part of the plant containing maximum amount of 1 and without employing tedious chromatographic procedures, is almost 300 times more than the yield reported in the literature using a method which employed tedious and time consuming Preparative Thin Layer Chromatography not suitable for isolating large amounts of the constituent.

The invention is described in detail by the examples given below which should not be construed to the limit of scope of the present invention.

EXAMPLE 1

The shade dried, powdered *Boerhavia diffusa* leaves (1 kg) were extracted with rectified spirit by hot continuous extraction in a Soxhlet apparatus for 32 hours. The rectified spirit was evaporated under reduced pressure to obtain a dark green mass, and this extract was triturated successively with hexane, chloroform and ethyl acetate. The residue left was dissolved in methanol and left in refrigerator overnight, the solid separated by filtration, crystallized with methanol, to obtain eupalitin 3-O-β-D-galactopyranoside (4.0 g).

EXAMPLE 2

The shade dried, powdered *Boerhavia diffusa* leaves (1 kg) were extracted with methanol by hot continuous extraction in a Soxhlet apparatus for 32 hours. The methanol was evaporated under reduced pressure to obtain a dark green mass, and this extract was triturated successively with hexane, chloroform and ethyl acetate. The residue left was dissolved in methanol and left in refrigerator overnight, the solid separated by filtration, crystallized with methanol, to obtain eupalitin 3-O-β-D-galactopyranoside (3.5 g).

EXAMPLE 3

The shade dried, powdered *Boerhavia diffusa* leaves (1 kg) were percolated with rectified spirit (4×41) for a period 64 hours. The rectified spirit was evaporated under reduced pressure to obtain a dark green mass, and this residue was triturated successively with hexane, chloroform and ethyl acetate. The residue left was dissolved in methanol and left in refrigerator overnight, filtered, the solid separated, crystallized with methanol, to provide eupalitin 3-O-β-D-galactopyranoside (2.8 g).

EXAMPLE 4

The shade dried, powdered *Boerhaavia diffusa* stems (1 kg) were extracted with rectified spirit by hot continuous extraction in a Soxhlet apparatus for 32 hours. The rectified spirit was evaporated under reduced pressure to obtain a residue, and this residue was triturated successively with hexane, chloroform and ethyl acetate. The residue left was dissolved in methanol and left in refrigerator overnight, the solid separated by filtration, crystallized with methanol, to obtain eupalitin 3-O-β-D-galactopyranoside (0.7 g).

EXAMPLE 5

The shade dried, powdered *Boerhavia diffuse* aerial parts (1 kg) was extracted with rectified spirit by hot continuous extraction in a Soxhlet apparatus for 32 hours. The rectified spirit was evaporated under reduced pressure to obtain a dark green mass, and this extract was triturated successively with hexane, chloroform and ethyl acetate. The residue left was dissolved in methanol and left in refrigerator overnight, the solid separated by filtration, crystallized with methanol, to provide eupalitin 3-O-β-D-galactopyranoside (1.2 g).

EXAMPLE 6

The shade dried, powdered *Boerhaavia diffusa* leaves (1 kg) was percolated with 80% aqueous methanol (4×4l) for a period 64 hours. The solvent was evaporated under reduced pressure to obtain a dark green mass, and this extract was triturated successively with hexane, chloroform and ethyl acetate. The residue left was dissolved in methanol and left in refrigerator overnight, filtered, the solid separated, crystallized with methanol, to obtain eupalitin 3-O-β-D-galactopyranoside (3.0 g).

ADVANTAGES

1. This is a novel process by which we can isolate eupalitin 3-O-(3-D-galactopyranoside.
2. The process being simple is particularly useful for quick isolation of the compound from the plant for all purposes.
3. Process utilizes highly economical raw material which is abundant in nature.
4. The concept used in the process makes it ideal and easy for scale up.
5. The process offers guaranteed yield as it has been standardized with respect to location of collection of plant material also.
6. The process does not prescribe any tedious chromatographic procedure for purification and isolation of the compound whereas the previous reported procedure involves the expensive, tedious and time consuming Preparative Thin Layer Chromatography yielding minute quantity of compound of formula 1.
7. The process offers an yield which is 300 times more than that reported in literature.

We claim:

1. A process for the isolation of 3-O-β-D-galactopyranoside of the formula 1 from aerial parts of *Boerhaavia diffusa*, comprising:
    (a) powdering the aerial parts of,
    (b) preparing an extract of the powdered aerial parts of with a protic solvent,
    (c) concentrating the extract obtained in step (b) above,
    (d) triturating the above said concentrated extract successively with a series of at least three organic solvents in order of increasing polarity, the solvents being selected from the group consisting of hexane, dichloromethane, chloroform, ethyl acetate, ethanol, methanol and aqueous methanol in order of increasing polarity to get an enriched bioactive fraction,
    (e) crystallizing and recrystallizing the bioactive fraction with methanol to obtain 3-O-β-D-galactopyranoside,

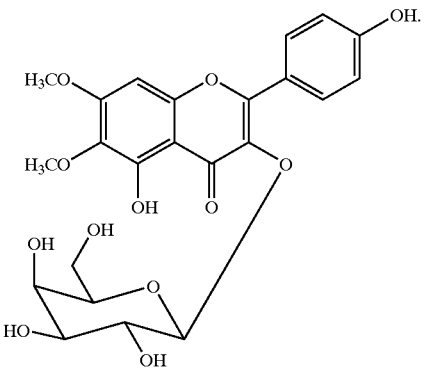

2. The process according to claim 1 wherein the aerial parts of *Boerhaavia diffusa* are selected from the group consisting of the leaves, the stems and a combination of the leaves and stems of *Boerhaavia diffusa*.

3. The process as claimed in according to claim 1 wherein the protic solvent used for the extraction in step (b) is selected from rectified spirit, methanol, and aqueous methanol.

4. The process according to claim 1 wherein the organic solvent used in step (d) is in the order of hexane, chloroform, and ethyl acetate.

5. The process according to claim 1 wherein said extraction of the powdered plant material with a protic solvent is carried out in a glass percolator or in a Soxhlet extractor.

* * * * *